United States Patent [19]

Kolobow et al.

[11] Patent Number: 6,027,516
[45] Date of Patent: *Feb. 22, 2000

[54] HIGHLY ELASTIC, ADJUSTABLE HELICAL COIL STENT

[75] Inventors: Theodor Kolobow, Rockville; Jeffrey Y. Wang, Gaithersburg, both of Md.

[73] Assignee: The United States of America as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/434,822

[22] Filed: May 4, 1995

[51] Int. Cl.⁷ .................................................. A61M 29/00
[52] U.S. Cl. .......................... 606/191; 606/108; 623/1; 604/96
[58] Field of Search ................................ 606/1, 108, 190, 606/191–198; 128/898; 623/1, 11, 12; 604/96–104

[56] References Cited

U.S. PATENT DOCUMENTS

| | | |
|---|---|---|
| 3,868,956 | 3/1975 | Alfidi et al. . |
| 4,512,338 | 4/1985 | Balko et al. . |
| 4,553,545 | 11/1985 | Maass et al. . |
| 4,665,918 | 5/1987 | Garza et al. . |
| 4,820,298 | 4/1989 | Leveen et al. . |
| 4,848,342 | 7/1989 | Kaltenbach . |
| 4,889,137 | 12/1989 | Kolobow . |
| 4,954,126 | 9/1990 | Wallsten . |
| 5,002,560 | 3/1991 | Machold et al. . |
| 5,015,232 | 5/1991 | Maglinte . |
| 5,147,370 | 9/1992 | McNamara et al. . |
| 5,201,901 | 4/1993 | Harada et al. . |
| 5,234,425 | 8/1993 | Fogarty et al. . |
| 5,246,445 | 9/1993 | Yachia et al. . |
| 5,342,300 | 8/1994 | Stefanadis et al. . |
| 5,372,600 | 12/1994 | Beyar et al. ............................ 606/194 |
| 5,476,505 | 12/1995 | Limon ..................................... 606/191 |
| 5,601,593 | 2/1997 | Freitag ................................... 606/198 |

OTHER PUBLICATIONS

Rossi, F., Kolobow, T., Foti, G., et al., Long–term cardiopulmonary bypass by peripheral cannulation in a model of total heart failure. J. Thorac Cardiovasc Surg 1990; 100:914–20.

Primary Examiner—Glenn K. Dawson
Attorney, Agent, or Firm—Townsend and Townsend and Crew LLP; Guy W. Chambers

[57] ABSTRACT

A highly elastic, adjustable helical coil stent (10) has a helical coil (20) which can be contracted around a small diameter catheter (12) for percutaneous insertion into a human body and then can be remotely expanded back to its original shape when positioned at the desired location within the human body. The helical coil is preferably formed of a metal alloy (25) with high elasticity, such as superelastic Nitinol, encased within an elastomer (26). The helical coil is affixed at its distal end to a catheter and affixed at its proximal end to a control tube (30). By rotating the control tube in one direction relative to the catheter (e.g., clockwise), the helical coil contracts and by rotating the control tube in the opposite direction (e.g., counterclockwise), the helical coil expands. The adjustable helical coil stent of the present invention is particularly useful for total or partial heart assist during heart bypass procedures. It can also be used, for example, as a stent for damaged blood vessels or other body conduits in either humans or animals.

21 Claims, 2 Drawing Sheets

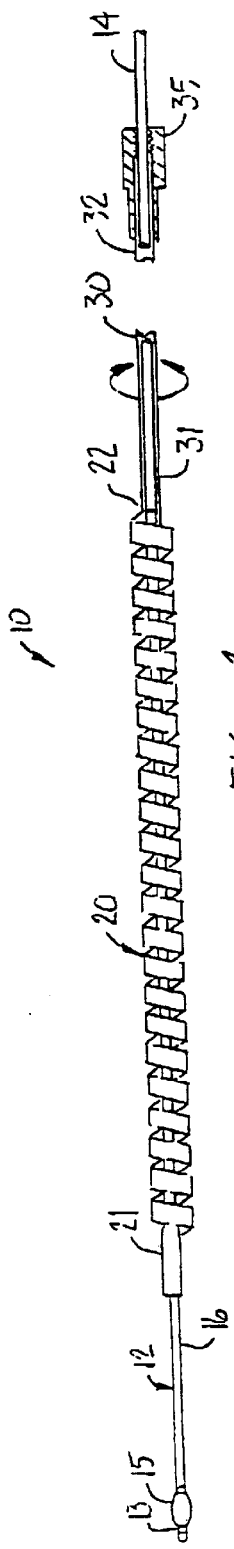
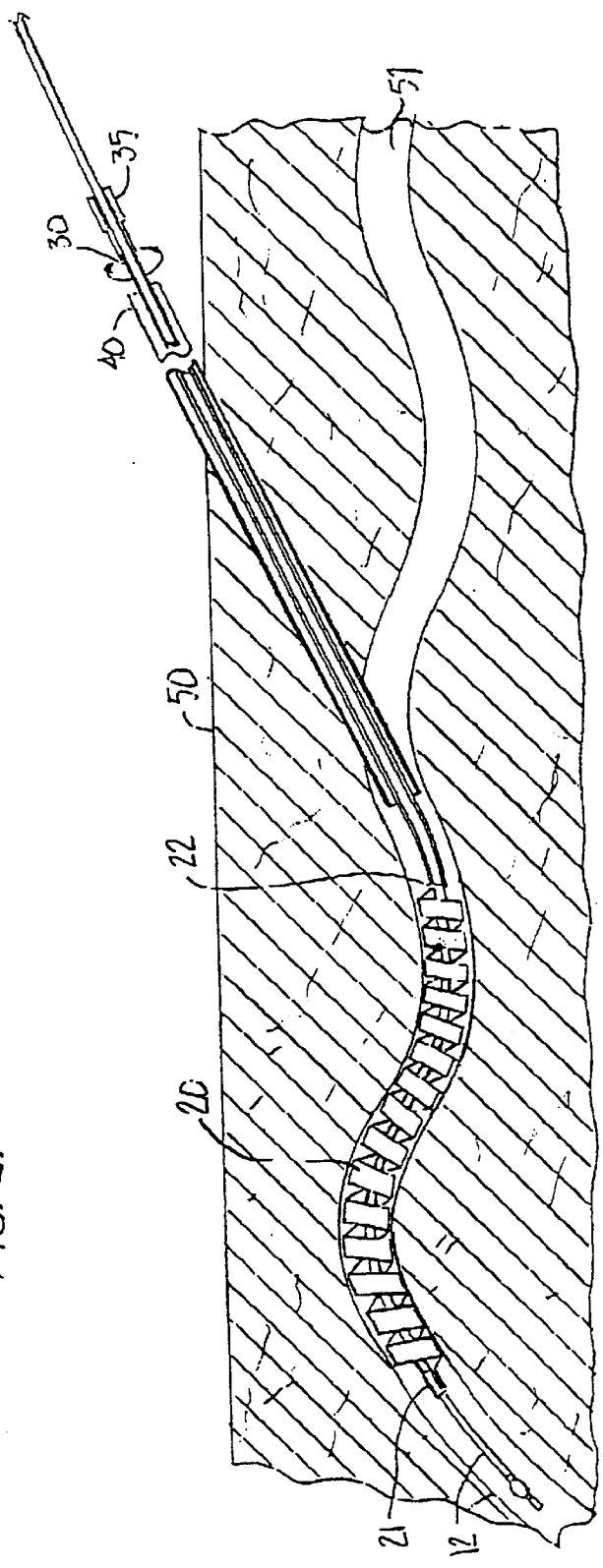
FIG. 1.
FIG. 2.
FIG. 3.

HIGHLY ELASTIC, ADJUSTABLE HELICAL COIL STENT

TECHNICAL FIELD OF THE INVENTION

The present invention relates to medical devices used to hold open blood vessels, heart valves and other conduits of the human body during a medical procedure. Specifically, a highly elastic, adjustable helical coil stent is disclosed whose coils can be contracted around a small diameter catheter for percutaneous insertion into a human body and then be remotely expanded back to its original shape when positioned at the desired location within the human body. such a highly elastic, adjustable helical coil stent is especially useful for total or partial heart assist during heart bypass procedures.

BACKGROUND OF THE INVENTION

It is sometimes necessary during medical procedures to insert a device into blood vessels, heart valves, urinary tracts or other conduits of the human body in order to either hold open or widen those conduits. These devices are generally referred to as "stents." A number of the stents known in the art take the form of a helical coil and are designed for permanent implantation. An example of such a permanently implantable helical coil stent is shown in U.S. Pat. No. 5,201,901, issued to Harada. In the Harada patent, a stent is constructed in one embodiment out of a unidirectional memory alloy, such as heat activated nickel-titanium alloy ("heat/cool Nitinol"), which is responsive to body heat. After such a stent is inserted into the appropriate location in the body with the aid of a guide wire or catheter, the body heat causes it to expand to a predetermined or "memorized" size. The guide wire or catheter is then withdrawn to allow the stent to remain permanently implanted.

In certain medical procedures where stents are needed, it would be impractical to leave the stent permanently implanted. One of these medical procedures is the heart bypass procedure with heart assist described in U.S. Pat. No. 4,889,137, issued to co-inventor Kolobow, the disclosures of which are incorporated by reference. In such a heart bypass procedure, a stent is used to temporarily keep one or both of the pulmonary and tricuspid valves partially or totally open. This stent is needed to provide effective decompression of the left heart during the heart bypass procedure in order to prevent the onset of potentially lethal forms of acute pulmonary edema. Of course, if the heart is to return to its normal function after the heart bypass procedure, it is necessary for the stent to be adjusted back to a contracted state and completely removed so that the heart valves can return to their normal function.

Several helical coil stents in the art have already been made to be temporary and adjustable. These include the temporary, adjustable helical coil stents of U.S. Pat. No. 4,553,545, issued to Maass, and of U.S. Pat. No. 5,342,300, issued to Stefanadis. In both the Stefanadis and Maass patents, adjustable helical coil stents are made of bare stainless steel. In his patent, Maass recognizes that thin stainless steel coils have a tendency in an expanded state to be mechanically unstable, even at the modest expansion ratios of 0.5 to 3.8 described in his specification. This instability results in the tilting or collapse of the coil after its operational expansion. Maass tries to address this problem by adding a cumbersome set of additional parts which he refers to as "rigidifying means."

What is needed in the art is a simple, highly elastic, adjustable helical coil stent which does not become mechanically unstable when placed in an expanded state. This is particularly needed for heart bypass procedures where the helical coil stent must be greatly compressed to be inserted into a narrow blood vessel and then reliably expanded to hold open a heart valve. The expansion ratios involved in such a heart bypass procedure can be significantly greater that the 0.5 to 3.8 range described by Maass.

What is also needed in the art is a simple, highly elastic, adjustable helical coil stent which will not promote blood clotting or blood vessel damage through the contact of sharp metallic surfaces with soft blood vessel tissue.

SUMMARY OF THE INVENTION

The present invention provides a simple, highly elastic, adjustable helical coil stent whose helical coils can be contracted around a small diameter catheter for percutaneous insertion into a human body and then be remotely expanded back to its original shape when positioned at the desired location within the human body. This adjustable helical coil stent is preferably formed of a metal alloy with high elasticity, such as superelastic Nitinol, and encased within an coated elastomer, such as a heparin coated polyester Hytrel elastomer, to help prevent blood clotting and damage soft tissue. The adjustable helical coil stent of the present invention has its helical coils affixed at their distal end to a catheter and affixed at their proximal end to a control tube. By rotating the control tube in one direction relative to the catheter, the adjustable helical coils can be made to contract. By rotating the control tube in the other direction, the adjustable helical coils can be made to expand. The adjustable helical coil stent of the present invention is particularly useful for total or partial heart assist during heart bypass procedures where high expansion ratios and delicate tissue are involved. It can also be used, for example, as a stent for blood vessels or other body conduits in either humans or animals.

BRIEF DESCRIPTION OF THE DRAWINGS

FIG. 1 shows a side view of the adjustable helical coil stent of the present invention.

FIG. 2 shows a detail cross-section of the helical coil itself.

FIG. 3 shows how the adjustable helical coil of the present invention can be percutaneously inserted into a human blood vessel.

DESCRIPTION OF THE SPECIFIC EMBODIMENTS

Figure 4:
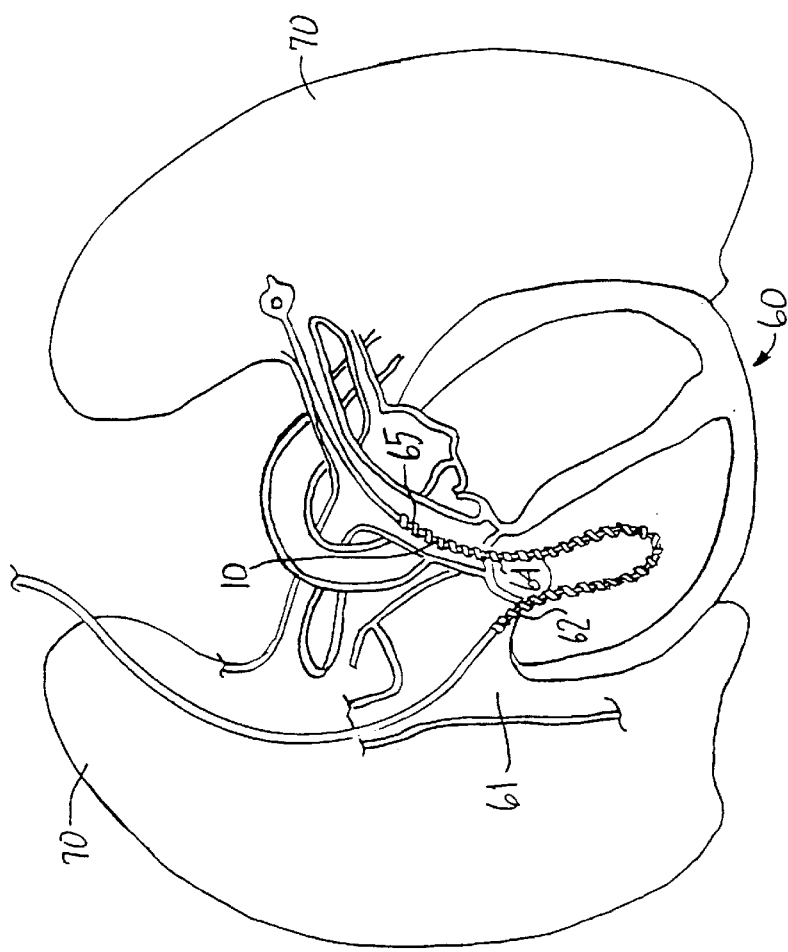
FIG. 4 shows use of the adjustable helical coil stent of the present invention for heart assist during a heart bypass procedure.

FIG. 1 shows a preferred form of adjustable helical coil stent 10 of the present invention. In this adjustable helical coil stent 10, a helical coil 20 is wrapped around a balloon catheter 12. The balloon catheter 12 features a flexible balloon 15 near its distal end 13 connected to a hollow, polymeric catheter shaft 16 of about 1 to 4 mm in diameter. This balloon catheter 12 is preferably a Swan Ganz type catheter. One of skill in the art will recognize, though, that other types of catheters could be used in the present invention, including multilayered catheters and catheters without balloons. The distal end 13 of the balloon catheter 12 of the present invention is preferably left open so that blood samples can be collected when the stent is in the body and blood temperature or pressure can be monitored.

The helical coil 20 shown in FIG. 1 has a distal end 21 and a proximal end 22. The distal end 21 of the helical coil 20 is permanently affixed to the shaft 16 of the balloon catheter 12. It can be preferably affixed by fusing the helical coil 20 and catheter 12 materials, by bonding them together with a permanent adhesive, such as a cyanoacrylate adhesive, or by mechanical attachment techniques. One preferred technique for bonding is to first adhere the helical coil 20 to the catheter 12 with cyanoacrylate adhesive and then wrap the bonded joint with a monofilament Kevlar fiber for extra strength.

At its proximal end 22, the helical coil 20 is affixed to the distal end 31 of a flexible, hollow control tube 30 as shown in FIG. 1. Again, the helical coil 20 is permanently affixed to this hollow control tube 30 through fusing, adhesive bonding or other means. One preferred technique is to fuse the helical coil 20 to the control tube 30 with heat and pressure and then wrap the fused joint with a monofilament Kevlar fiber for extra strength. The hollow control tube 30 is placed concentrically over the balloon catheter 12 so that it can move independently of the balloon catheter 12. The hollow control tube 30 is permanently affixed at its proximal end 32 to an adjustable seal 35. Using this arrangement, the control tube 30 and adjustable seal 35 can be rotated in one direction relative to the catheter 12 to contract the helical coil (e.g., clockwise) and rotated in the other direction (e.g., counterclockwise) to expand the helical coil.

In FIG. 2, a cross-section of the helical coil 20 is shown. At the center of this helical coil 20 is a wire 25 made out of a highly elastic metal alloy, such as a heat treated, superelastic nickel-titanium alloy ("superelastic Nitinol"). This superelastic Nitinol can be purchased from Fort Wayne Metals of Fort Wayne, Ind. It is important to distinguish this preferred "superelastic Nitinol" from the "heat/cool Nitinol" of prior art helical coil stents. The inventors have found that helical coils made of superelastic Nitinol can have expansion ratios over 50 and are not significantly affected by body heat like "heat/cool Nitinol". In this context, the "expansion ratio" is defined as the diameter of maximum helical coil expansion during operation divided by the diameter of maximum helical coil contraction during operation. Unlike helical coil stents of the prior art, it is an object of the present invention to have precise control over the dimensions of the helical coil by not having such dimensions vary significantly with the ambient temperature.

For heart assist during a heart bypass procedure, the inventors have found that the superelastic Nitinol wire 25 preferably has cross-sectional dimensions of about 0.10 mm by 1.0 mm. When the adjustable helical coil stent of the present invention is used in smaller body conduits, such as coronary arteries, use of a finer superelastic Nitinol wire is preferred. By contrast, when the adjustable helical coil stent of the present invention is used in larger body conduits, such as the esophagus or trachea, either a wider and thicker Nitinol wire can be used or a plurality of finer superelastic Nitinol wires is preferred.

To reduce the risk of blood clotting and inflammation to the body tissue through which the helical coil stent 10 is passing, the helical coil wire 25 shown in FIG. 2 is preferably encased within a coated elastomeric sheathing 26. The inventors have found that a variety of materials can be used for the elastomeric sheathing 26 such as polyester Hytrel, polyurethane and silicone rubber. To prevent blood clotting, this elastomeric sheathing 26 is preferably coated with heparin or a heparin complex. Use of a slightly porous elastomer for the sheathing 26, rather that a solid elastomeric material, can also help reduce the risk of blood clotting.

With an elastomeric sheathing 26 used to encase wire 25 as shown in FIG. 2, the full cross-sectional dimensions of the helical coil used for heart assist during a heart bypass procedure are preferably from about 4.0 to 8.0 mm in width and 0.1 to 0.2 mm in thickness. This width and thickness can, of course, vary depending upon the application in much the same way that the thickness of the wire varies. The length of coil used for such a heart bypass procedure is preferably about 3.0 to 8.0 cm. Also, while the coil shown in FIG. 2 has rectangular cross-sections for both the wire 25 and elastomeric sheathing 26, those of skill in the art will readily recognize that the wire 25 and sheathing can have other cross-sectional shapes, such as circular or oval.

FIG. 3 shows an adjustable helical coil stent of the present invention after being inserted percutaneously into a blood vessel. The preferred technique for such insertion is to first insert a syringe (not shown) through the skin until it reaches the desired blood vessel. A dilator (not shown) is then used to expand the size of the hole created by the syringe. The dilator should expand the hole wide enough that an introducer sheath 40 can then be inserted. With helical coil stents from the prior art, the dilator would typically need to expand the hole wide enough to accommodate an introducer sheath with an approximate outside diameter of 13 mm, about 39 French, a very formidable task. Due to the high elasticity of the alloy wire 25 used in the present helical coil stent invention, though, a much smaller diameter introducer sheath 40 of approximately 4.6 mm, about 14 French, can be used instead.

Once the introducer sheath 40 shown in FIG. 3 is in place, the helical coil stent 10 of the present invention can be inserted. Before such insertion, the helical coil 20 should be contracted around the balloon catheter 12 by rotating the control device 30 in an appropriate direction relative to the balloon catheter 12 (e.g., in a clockwise direction). The helical coil 20 must be contracted to a diameter which is less than the internal diameter of the introducer sheath 40. If the helical coil stent 10 needs to be moved in the direction of blood flow, it is also advantageous to inflate the balloon 15 of balloon catheter 12 so that the blood flow can assist the progression of the helical coil stent 10 by creating an upstream pressure against the balloon 15. The control tube 30 and adjustable seal 35 of the helical coil stent should fit snugly, yet movably, against the inside of the introducer sheath 40 in order to prevent both blood from exiting the control tube and spontaneous uncoiling of the helical coil 20. For these same reasons, the control tube 30 and adjustable seal 35 should also fit snugly, yet movably, against the outside of the balloon catheter shaft 16. To achieve this type of snug fit, the control tube 30 and adjustable seal 35 are preferably made of a pliable, polymeric material, such as silicone rubber.

When the helical stent is moved into its desired position in the blood vessel 51, as shown in FIG. 3, or other body conduit, the helical coil can be expanded to an appropriate diameter by rotating the control device 30 relative to the balloon catheter 12 in the appropriate direction (e.g., in a counterclockwise direction). Both the positioning and diameter of the helical coil stent 10 can be checked with a fluoroscope or X-ray. It is also appropriate when the helical coil stent has been appropriately positioned to deflate the balloon 15 of the balloon catheter 12.

To remove the helical coil stent 10 of the present invention from a blood vessel or other body conduit at the conclusion of a medical procedure, one begins by contracting the helical coil 20 to the point where it is wrapped tightly around the balloon catheter 12. The helical coil stent 10 can then be slowly withdrawn by pulling on the adjustable seal 35. When the helical coil stent 10 is fully withdrawn from the introducer sheath 40, the introducer sheath 40 itself can then be withdrawn and the skin bandaged.

As previously mentioned, a preferred application for the helical coil stent 10 of the present invention is as a heart assist during heart bypass procedures. During such a procedure, the helical coil stent 10 of the present invention can be introduced into the body through the internal or external jugular vein (not shown). It is preferably introduced with the balloon 15 of balloon catheter 12 being inflated to a diameter of about 7 to 9 mm. As shown if FIG. 4, the helical coil stent 10 can then be threaded past the lungs 70, then through the right atrium 61 of the heart 60, through the right atrioventricular or tricuspid valve 62 of the right ventricle, through the pulmonary valve 64 and finally into the pulmonary artery 65 until its distal end 13 reaches the left or right stem of the pulmonary artery 65. At that point, the pulmonary artery 65 narrows to the point that the balloon diameter becomes greater than the diameter of the pulmonary artery 65. With insertion of the helical coil stent 10 stopped at this point, the helical coil 20 should be correctly positioned inside one or both of the pulmonary valve 65 and tricuspid valve 62. The correctness of this positioning can be checked with a fluoroscope or X-ray.

With the correct positioning of the helical coil stent 10 confirmed, the helical coils 20 can be expanded to an appropriate diameter through appropriate rotation of the control tube 30 relative to the balloon catheter 12 (e.g., in a counterclockwise direction). In the case of a relatively healthy heart, the helical coils 20 can be expanded to a lesser diameter to hold one or both of the pulmonary valve 65 and tricuspid valve 62 partially open. By contrast, in the case of the severest forms of heart failure, the helical coils 20 can be expanded to a greater diameter to hold one or both of the pulmonary valve 65 and tricuspid valve 62 completely open. Also, the helical coil stent 10 of the present invention allows adjustment of valve opening size to be made during the course of the heart assist. The helical coil stent 10 of the present invention is designed to be left in place for days or even weeks, depending upon how long the heart valves need to be left open. While the helical coil stent 10 of the present invention is in place, an external artificial heart machine can be used to pump blood throughout the body. Removal of the helical coil stent 10 can be easily accomplished by first rotating the control tube 30 (e.g., in a clockwise manner) until the helical coil 20 is contracted tightly against the catheter 12 and then slowly pulling the helical coil stent 10 out of the body.

As those skilled in the art will readily recognize, the helical coil stent of the present invention can provide heart assist for extended periods of time without thoracotomy, permanent implantation of a heart assist device or permanent implantation of an artificial heart. Because the control tube 30 for the present helical coil stent 10 is located outside the body, adjustments can easily be made to the diameter of the helical coils 20 while in operation. When used in conjunction with an external artificial heart machine, the present helical coil stent offers a means for the heart to rest and recover without resorting to pharmacologic agents. Corrective surgery can then be performed as and when needed with better prospects for more rapid recovery. The present helical coil stent, when used as a heart assist, thus provides a simple and rapid way of unloading the heart while allowing optimal perfusion to the heart and other organ systems.

Figure 5:
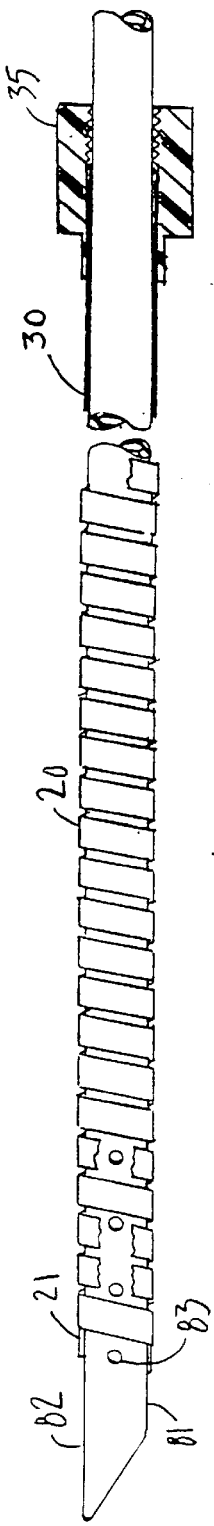
FIG. 5 shows an alternative adjustable helical coil stent of the present invention configured as a drainage catheter.

Turning now to FIG. 5, an alternative embodiment of the present invention is shown. In this figure, the helical coil stent is shown configured as a drainage stent 80 which can be used to keep a conduit open while it is being drained. The principal difference between this alternative embodiment and the earlier preferred embodiment is the configuration of the catheter 81. In this case, a hollow drainage catheter 81 with a blunted tip 82 and drainage holes 83 is used rather than the balloon catheter 12 of the earlier preferred embodiment. The helical coil 20, nonetheless, continues to be permanently affixed to the drainage catheter 81 at its distal end 21 and permanently affixed to a control tube 30 at its proximal end. In operation, the helical coil 20 is again contracted tightly around the drainage catheter 81 when percutaneously inserted and, when positioned at the appropriate place in the conduit, expanded through appropriate rotation of the control tube 30 and adjustable seal 35 (e.g., counterclockwise). Drainage then occurs as fluid seeps through the catheter drainage holes 83 and out of the proximal end of the catheter. When the drainage procedure is completed, the drainage stent can be removed by contracting the helical coil 20 tightly around catheter 81 through appropriate rotation of the control tube 30 (e.g., clockwise) and slowly pulling the contracted drainage stent 80 out of the body.

In the foregoing specification, the invention has been described with reference to specific preferred embodiments and methods. It will, however, be evident to those of skill in the art that various modifications and changes may be made without departing from the broader spirit and scope of the invention as set forth in the appended claims. The specification and drawings are, accordingly, to be regarded in an illustrative, rather than restrictive, sense; the invention being limited only by the appended claims.

What is claimed is:

1. An adjustable helical coil stent comprising:
   (a) a helical coil having proximal and distal ends, said helical coil formed of a thin superelastic nickel-titanium alloy wire encased within an elastomer having a cross-sectional width which is about four to eight times greater than the width of said wire;
   (b) a catheter to which said helical coil is permanently affixed at said distal end; and,
   (c) a control tube, to which said helical coil is permanently affixed at said proximal end, said control tube used for expanding and contracting said helical coil through rotation of said control tube relative to said catheter and for later removal of said helical coil.

2. The adjustable helical coil stent of claim 1 wherein said helical coil can be contracted by rotating said control tube clockwise relative to said catheter.

3. The adjustable helical coil stent of claim 1 wherein said helical coil can be expanded away from said catheter by rotating said control tube counterclockwise relative to said catheter.

4. The adjustable helical coil stent of claim 1 wherein said elastomer is polyester Hytrel.

5. The adjustable helical coil stent of claim 1 wherein said elastomer is coated with heparin or a heparin complex.

6. The adjustable helical coil stent of claim 1 wherein said catheter is a balloon catheter.

7. The adjustable helical coil stent of claim 1 wherein said catheter is a drainage catheter.

8. The adjustable helical coil stent of claim 1 wherein said helical coil is about 3.0 to 8.0 cm. in length and has cross-sectional dimensions of about 4.0 to 8.0 mm in width and 0.1 to 0.2 mm in thickness.

9. The adjustable helical coil stent of claim 1 having a stable expansion ratio of over 50 to 1.

10. The adjustable helical coil stent of claim 1 wherein said catheter is inserted concentrically within said control tube but is free to rotate independent of said control tube.

11. The adjustable helical coil stent of claim 10 wherein the proximal end of said control tube is affixed to an adjustable seal.

12. An adjustable helical coil stent comprising:
   (a) a helical coil having proximal and distal ends, said helical coil formed of a thin superelastic nickel-titanium alloy wire encased within an elastomer having a cross-sectional width which is about four to eight times greater than the width of said wire;
   (b) a balloon catheter to which said helical coil is permanently affixed at said distal end; and,
   (c) a control tube concentrically overlaying said balloon catheter and to which said helical coil is permanently affixed at said proximal end, said control tube used for expanding and contracting the helical coil through rotation of said control tube relative to said catheter and for later removal of said helical coil.

13. A method for heart assist during heart bypass procedure in a human body comprising the steps of:
   (a) selecting an adjustable helical coil stent comprising:
      (i) a helical coil having proximal and distal ends, said helical coil formed of a thin superelastic nickel-titanium alloy wire surrounded by an elastomer having a cross-sectional width which is about four to eight times greater than the width of said wire;
      (ii) a catheter to which said helical coil is permanently affixed at said distal end; and,
      (iii) a control tube to which said helical coil is permanently affixed at said proximal end, said control tube used for expanding and contracting the helical coil through rotation of said control tube relative to said catheter;
   (b) percutaneously inserting said adjustable helical coil stent, with the helical coil in a contracted position, into a blood vessel leading to the heart;
   (c) continuing to insert said adjustable helical coil stent until the helical coil is located within one or more chosen heart valves;
   (d) adjusting said adjustable helical coil stent until said helical coil is in an expanded position which holds said chosen heart valve(s) open to a desired degree;
   (e) performing heart assist;
   (f) adjusting said adjustable helical coil stent until said helical coil is back in a contracted position; and,
   (g) removing said adjustable helical coil stent from said human body.

14. The method of claim 13 wherein said one or more chosen heart valves includes the pulmonary valve.

15. The method of claim 13 wherein said one or more chosen heart valves includes the tricuspid valve.

16. The method of claim 13 wherein said helical coil can be contracted by turning said control tube clockwise relative to said catheter.

17. The method of claim 13 wherein said helical coil can be expanded by turning said control tube counterclockwise relative to said catheter.

18. The method of claim 13 wherein said elastomer is polyester Hytrel.

19. The method of claim 13 wherein said elastomer is coated with heparin or a heparin complex.

20. The method of claim 13 wherein said catheter is a balloon catheter.

21. A method for draining fluids from a conduit in a human body comprising the steps of:
   (a) selecting an adjustable helical coil stent comprising:
      (i) a helical coil having proximal and distal ends, said helical coil formed of a thin superelastic nickel-titanium alloy wire surrounded by an elastomer having a cross-sectional width which is about four to eight times greater than the width of said wire;
      (ii) a drainage catheter to which said helical coil is permanently affixed at said distal end; and,
      (iii) a control tube to which said helical coil is permanently affixed at said proximal end, said control tube used for expanding and contracting the helical coil through rotation of said control tube relative to said catheter;
   (b) percutaneously inserting said adjustable helical coil stent in a contracted position into said conduit;
   (c) adjusting said adjustable helical coil stent until said helical coil is in an expanded position which holds said damaged conduit open;
   (d) allowing fluids to drain through said drainage catheter and out of said human body;
   (e) adjusting said adjustable helical coil stent until said helical coil is back in a contracted position; and, (f) removing said adjustable helical coil stent from said human body.

* * * * *